(12) United States Patent
Yuyama et al.

(10) Patent No.: US 11,319,422 B2
(45) Date of Patent: May 3, 2022

(54) PHOTOCATALYST TRANSFER FILM AND PRODUCTION METHOD THEREOF

(71) Applicant: SHIN-ETSU CHEMICAL CO., LTD., Tokyo (JP)

(72) Inventors: Masahiro Yuyama, Kamisu (JP); Manabu Furudate, Kamisu (JP); Tomohiro Inoue, Kamisu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 100 days.

(21) Appl. No.: 17/043,491

(22) PCT Filed: Mar. 26, 2019

(86) PCT No.: PCT/JP2019/012718
§ 371 (c)(1),
(2) Date: Sep. 29, 2020

(87) PCT Pub. No.: WO2019/198484
PCT Pub. Date: Oct. 17, 2019

(65) Prior Publication Data
US 2021/0053029 A1    Feb. 25, 2021

(30) Foreign Application Priority Data
Apr. 12, 2018  (JP) .............................. JP2018-076980

(51) Int. Cl.
| | | |
|---|---|---|
| B01J 21/06 | (2006.01) | |
| C08J 7/043 | (2020.01) | |
| C08J 7/056 | (2020.01) | |
| B01J 35/00 | (2006.01) | |
| B05D 5/06 | (2006.01) | |
| B05D 7/24 | (2006.01) | |
| B32B 27/28 | (2006.01) | |
| B32B 27/36 | (2006.01) | |
| B32B 37/00 | (2006.01) | |
| C08J 7/04 | (2020.01) | |
| C09D 5/16 | (2006.01) | |
| C09D 183/00 | (2006.01) | |

(52) U.S. Cl.
CPC ............. *C08J 7/043* (2020.01); *B01J 21/063* (2013.01); *B01J 35/004* (2013.01); *B05D 5/061* (2013.01); *B05D 7/24* (2013.01); *B32B 27/283* (2013.01); *B32B 27/36* (2013.01); *B32B 37/025* (2013.01); *C08J 7/04* (2013.01); *C08J 7/0427* (2020.01); *C08J 7/056* (2020.01); *C09D 5/1618* (2013.01); *C09D 5/1693* (2013.01); *C09D 183/00* (2013.01); *B05D 2201/02* (2013.01); *B05D 2401/20* (2013.01); *B05D 2601/22* (2013.01); *B05D 2601/24* (2013.01); *B05D 2601/28* (2013.01); *B32B 2264/1022* (2020.08); *B32B 2264/1051* (2020.08); *B32B 2264/301* (2020.08); *B32B 2307/412* (2013.01); *B32B 2307/7145* (2013.01); *B32B 2309/02* (2013.01); *B32B 2311/08* (2013.01); *B32B 2367/00* (2013.01); *B32B 2383/00* (2013.01)

(58) Field of Classification Search
CPC ...... B01J 21/063; B01J 35/004; C09D 183/00
See application file for complete search history.

(56) References Cited

U.S. PATENT DOCUMENTS

| | | | |
|---|---|---|---|
| 2016/0288091 | A1 | 10/2016 | Fukushima et al. |
| 2016/0288092 | A1 | 10/2016 | Fukushima et al. |
| 2020/0230575 | A1 | 7/2020 | Furudate et al. |

FOREIGN PATENT DOCUMENTS

| | | |
|---|---|---|
| JP | 2000-51708 A | 2/2000 |
| JP | 2001-260597 A | 9/2001 |
| JP | 2004-183030 A | 7/2004 |
| JP | 2005-60444 A | 3/2005 |
| JP | 2005-131552 A | 5/2005 |
| JP | 2005-212446 A | 8/2005 |
| JP | 2008-260684 A | 10/2008 |
| JP | 2009-120767 A | 6/2009 |
| JP | 2010-247450 A | 11/2010 |
| JP | 2013-32474 A | 2/2013 |
| JP | 2013-99919 A | 5/2013 |
| JP | 2015-57491 A | 3/2015 |
| JP | 2017-61667 A | 3/2017 |
| JP | 6200571 B1 * | 9/2017 |
| WO | WO 01/25362 A1 | 4/2001 |
| WO | WO 2018/012240 A1 | 1/2018 |

OTHER PUBLICATIONS

Machine translation of JP-6200571-B1 originally published Sep. 2017 to Oki (Year: 2017).*
Caplan et al., Antimicrobial activity of copper and silver nanofilms on nosocomial bacterial species, 2010, Roumanian Archives of Microbiology and Immunology, vol. 69, pp. 204-212 (Year: 2010).*
International Search Report (PCT/ISA/210) issued in PCT/JP2019/012718, dated Jul. 2, 2019.

(Continued)

*Primary Examiner* — Coris Fung
*Assistant Examiner* — Ritu S Shirali
(74) *Attorney, Agent, or Firm* — Birch, Stewart, Kolasch & Birch, LLP

(57) ABSTRACT

Provided are a photocatalyst transfer film allowing a photocatalyst layer that is uniform, highly transparent, and exhibits an antimicrobial property in dark places to be transferred to the surfaces of various transfer base materials; and a production method thereof. The photocatalyst transfer film has, on a base film, a photocatalyst layer containing a titanium oxide particle-containing photocatalyst, antimicrobial metal-containing alloy particles, a silicon compound and a surfactant. The production method of the photocatalyst transfer film includes applying a photocatalyst coating liquid to a base film; and performing drying. The photocatalyst coating liquid contains a titanium oxide particle-containing photocatalyst, antimicrobial metal-containing alloy particles, a silicon compound, a surfactant and an aqueous dispersion medium.

11 Claims, No Drawings

(56) References Cited

OTHER PUBLICATIONS

Kawakami et al., "Antibacterial Properties of Metallic Elements for Alloying Evaluated with Application of JIS Z 2801:2000," ISIJ International, vol. 48, No. 9, 2008, pp. 1299-1304.
Miyano et al., "Evaluation of Antibacterial Ability of Some Pure Metals," Tetsu-to-Hagane, vol. 93, No. 1, 2007, pp. 57-65.
Written Opinion of the International Searching Authority (PCT/ISA/237) issued in PCT/JP2019/012718, dated Jul. 2, 2019.
Office Action dated Mar. 23, 2021, in Japanese Patent Application No. 2020-513169.

* cited by examiner

PHOTOCATALYST TRANSFER FILM AND PRODUCTION METHOD THEREOF

TECHNICAL FIELD

The present invention relates to a transfer film used to produce a base material having a photocatalyst on its surface; and a production method thereof. Particularly, the invention relates to a photocatalyst transfer film capable of yielding a highly transparent photocatalyst thin film exhibiting a property such as an antimicrobial property.

BACKGROUND ART

A photocatalyst film laminated on the surface of a base material has been utilized for purposes such as cleaning, deodorizing and causing an antimicrobial effect on the base material surface, because a photocatalytic metal compound contained in the photocatalyst film, such as titanium oxide, is capable of decomposing organic substances when irradiated with an ultraviolet light-visible light and thus exhibiting a hydrophilic property.

In recent years, photocatalyst materials have gained attention as inorganic antimicrobial-antifungal agents, and are now gradually being put to practical use for purposes such as cleaning, deodorizing and causing an antimicrobial effect on base material surfaces. The photocatalytic reaction is a reaction caused by excited electrons and holes occurring as a result of a photocatalytic metal compound such as titanium oxide absorbing lights. The mechanism for acting as an antimicrobial agent is assumed as such that the excited electrons and holes that have been generated on the surface of a photocatalytic metal compound by the photocatalytic reaction will contribute to an oxidation-reduction reaction with the oxygen and water adsorbed to the surface of the photocatalytic metal compound, an active species thus generated will then act on microorganisms to annihilate them by causing damages to the cell membranes thereof, or even eventually decompose those microorganisms by acting on them for a long period of time. Thus, it can be said that the benefits of a photocatalyst material include, for example, the fact that it is effective on a wide variety of organisms such as fungi and also less likely to produce resistant bacteria, and the fact that the material hardly deteriorates with time.

However, since the photocatalytic reaction is caused by irradiation with lights in the ultraviolet region (wavelength 10 to 400 nm) or lights in the visible region (wavelength 400 to 800 nm), the effects thereof cannot be technically achieved in dark places that are not exposed to a natural or artificial light(s). Meanwhile, since bacteria and fungi (molds) can proliferate even without lights, there is demanded a photocatalyst material capable of exhibiting an antimicrobial-antifungal property even in dark places that are not exposed to lights in the case of a product requiring a certain property to last for a desired period of time, such as an antimicrobial-antifungal product.

In order to address the above problem, a photocatalyst material with an enriched photocatalytic function is being considered by combining a photocatalyst with an antimicrobial-antifungal agent other than a photocatalyst. Since a photocatalyst decomposes organic substances, it is appropriate that an inorganic antimicrobial-antifungal agent be used if a photocatalyst is used in combination with an antimicrobial-antifungal agent other than a photocatalyst. For example, JP-A-2000-051708 and JP-A-2008-260684 (Patent documents 1 and 2) disclose that an antimicrobial property and antifungal property in dark places can be achieved by adding silver, copper or the like as an antimicrobial-antifungal component to titanium oxide as a photocatalyst.

In general, a photocatalyst is used in a manner such that photocatalyst particles are to be dispersed in a solvent, followed by mixing a film-forming component(s) thereinto to produce a coating material, and then applying such coating material to a base material. However, as described above, practical problems have often occurred as a result of adding metal components such as silver, copper and zinc to improve the antimicrobial-antifungal capability. That is, as a method for supporting metals such as silver, copper and zinc; or even compounds thereof, it is not preferable to support them by reacting a photocatalyst particle powder with a metal raw material(s) because a great effort needs to be made afterward to disperse the reacted ingredients in a solvent. Further, if adding a metal raw material(s) to a dispersion liquid with photocatalyst particles already being dispersed therein, a dispersion stability of the photocatalyst particles will be inhibited, which will cause agglomeration in a way such that it is often difficult to achieve a practically required transparency when forming such a type of photocatalyst thin film on various base materials.

In addition, in a method for producing antimicrobial-antifungal metal-containing photocatalyst particles by adding metals such as silver, copper and zinc or even compounds thereof to a photocatalyst as a raw material and then performing heat treatment, a photocatalytic function achieved will deteriorate due to an impaired crystallinity of the photocatalyst particles, or part of the antimicrobial-antifungal metal(s) will not emerge as being covered by titanium oxide, thus causing a problem of achieving an impaired antimicrobial-antifungal property.

Further, a photocatalyst layer has a low film forming property as being composed of nanoparticles, thus making it difficult to maintain a surface film. It is now being considered that the adhesion of a film may be improved by adding a silicone-based binder or the like to a resin. However, there has been a problem that even an organic binder component(s) will decompose due to the oxidation decomposition effect of a photocatalyst, thus leading to an inferior sustainability of a photocatalyst film. Moreover, since certain types of base materials have a low smoothness, it is difficult to form a uniform photocatalyst film on a base material.

As a method for forming a photocatalyst on the surface of a base material, there is employed a method where a photocatalyst-containing coating liquid is directly applied to the surface of a base material by a coating method such as spray coating, roll coating or brush coating, followed by performing drying. However, a problem with such method is that it is inferior in productivity.

Meanwhile, it is known that a transfer method using a transfer sheet or transfer film with a photocatalyst layer already being formed thereon is superior in productivity, and that such transfer method allows a uniform film to be formed due to a high conformability to a base material surface.

JP-A-2001-260597 (Patent document 3) discloses a transfer film with a photocatalyst layer, an inorganic protective layer and an organic adhesive layer being integrally laminated on a base film. Further, WO01/025362 (Patent document 4) discloses a transfer film or sheet with a photocatalyst layer and an adhesive layer being laminated on the surface of a film-shaped or sheet-shaped base material.

However, in order to improve a transferability, these transfer sheets or films are required to have a laminated structure composed of at least three layers, which has led to a problem that the productivity of these transfer sheets or films is poor.

As a photocatalyst, since it is required that only a small degree of change in appearance be observed after forming a film on the base material, it is desired that there be used a photocatalyst dispersion liquid with a high transparency. JP-A-2005-131552 (Patent document 5) discloses a transfer sheet comprised of a transparent photocatalyst layer-forming composition. Here, while it is difficult to apply such photocatalyst coating liquid as a highly transparent aqueous dispersion to an organic film due to the influence of a surface tension, it is also conceivable to lower the surface tension of the liquid by mixing a solvent thereinto before performing coating. However, the problem is that transparency may be impaired as photocatalyst particles may be precipitated depending on the type of the solvent, or that it is difficult to form a uniform film in actual production steps as the coating film may contract in the midst of a drying procedure due to differences in evaporation rates in the mixed liquid.

Meanwhile, while a film forming capability may be improved by mixing an organic resin binder component(s) into a photocatalyst, there exists a problem that a photocatalytic activity will be impaired as the organic resin binder component(s) will cover the photocatalyst particles. Further, in order to make transfer processing easier, there may be used a type of film with a silicone layer being provided on the mold release film, and a photocatalyst layer being further provided thereon. However, a problem with this type of film is, for example, such that an insufficient photocatalytic activity will be achieved as a resin layer comprised of a small amount of silicone or the like will cover the surface after transfer.

PRIOR ART DOCUMENTS

Patent Documents

Patent document 1: JP-A-2000-051708
Patent document 2: JP-A-2008-260684
Patent document 3: JP-A-2001-260597
Patent document 4: WO01/025362
Patent document 5: JP-A-2005-131552

SUMMARY OF THE INVENTION

Problems to be Solved by the Invention

Therefore, it is an object of the present invention to provide a photocatalyst transfer film that has a favorable molding processability, and is capable of yielding a highly transparent photocatalyst thin film exhibiting an antimicrobial property even in dark places; and a production method thereof.

Means to Solve the Problems

In order to solve the aforementioned problems, the inventors of the present invention diligently conducted a series of studies and completed the invention as follows. That is, the inventors found that the photocatalyst transfer film described below could be used to easily produce a highly transparent photocatalyst film capable of being uniformly formed on the surfaces of various base materials, and exhibiting an antimicrobial property.

Here, in this specification, the term "antimicrobial property" may refer to a property for restricting the proliferation of microorganisms including bacteria and fungi (molds).

Thus, the present invention is to provide the following photocatalyst transfer film and a production method thereof.

A photocatalyst transfer film having, on a base film, a photocatalyst layer containing a titanium oxide particle-containing photocatalyst, antimicrobial metal-containing alloy particles, a silicon compound and a surfactant.

The photocatalyst transfer film according to [1], wherein the silicon compound is a hydrolysis condensate of a tetra-functional silicon compound, the hydrolysis condensate being obtained under the presence of an organic ammonium salt.

The photocatalyst transfer film according to [1] or [2], wherein the surfactant is an acetylene-based surfactant.

The photocatalyst transfer film according to any one of [1] to [3], wherein an antimicrobial metal(s) contained in the antimicrobial metal-containing alloy particles is at least one kind of metal selected from the group consisting of silver, copper and zinc.

The photocatalyst transfer film according to any one of [1] to [4], wherein the antimicrobial metal-containing alloy particles at least contain silver.

The photocatalyst transfer film according to any one of [1] to [5], wherein the antimicrobial metal(s) contained in the antimicrobial metal-containing alloy particles is in an amount of 1 to 100% by mass with respect to a total mass of the alloy particles.

The photocatalyst transfer film according to any one of [1] to [6], wherein a dispersed particle size of a particle mixture of the two kinds of particles which are the titanium oxide particles and the antimicrobial metal-containing alloy particles is 5 to 100 nm in terms of a 50% cumulative distribution diameter $D_{50}$ on volume basis that is measured by a dynamic light scattering method using a laser light.

The photocatalyst transfer film according to any one of [1] to [7], wherein the photocatalyst layer has a thickness of 20 to 300 nm.

The photocatalyst transfer film according to any one of [1] to [8], wherein the base film has a thickness of 12.5 to 100 μm.

The photocatalyst transfer film according to any one of [1] to [9], wherein a protective layer containing a silicon compound is further laminated on the photocatalyst layer.

A method for producing a photocatalyst transfer film, comprising: applying a photocatalyst coating liquid to a base film, the photocatalyst coating liquid containing a titanium oxide particle-containing photocatalyst, antimicrobial metal-containing alloy particles, a silicon compound, a surfactant and an aqueous dispersion medium; and performing drying.

Effects of the Invention

According to the photocatalyst transfer film of the present invention, a uniform and highly transparent photocatalyst layer exhibiting an antimicrobial property in dark places can be processed and transferred to the surfaces of various base materials.

MODE FOR CARRYING OUT THE INVENTION

Described hereunder are a photocatalyst transfer film of the present invention and a method for producing the same.
[Photocatalyst Transfer Film]
<Base Film>
As a base film used in the photocatalyst transfer film of the present invention, there may be used those known as base films for transfer. Examples of such base films include plastic films such as a polyethylene terephthalate (PET) film, a polyethylene naphthalate (PEN) film, a polyethylene (PE) film, a polyimide film, an acrylic film, a vinyl chloride film, a cast polypropylene (CPP) film, a biaxially oriented polypropylene (OPP) film and a polyamide film. A PET film and an OPP film are particularly preferred.

As the base film, a plastic film that has not yet been subjected to a surface treatment is particularly preferred in terms of outer appearance and photocatalytic effect after transfer processing.

Further, it is preferred that the base film have an arithmetic average roughness Ra of 0.01 to 3 µm, more preferably 0.01 to 1 µm, when measured by a 3D laser microscope. It is not preferable when the Ra value of the base film is smaller than 0.01 µm, because it will be difficult to produce a uniform film. Further, it is also not preferable when the Ra value of the base film is greater than 3 µm, because the photocatalytic effect after transfer will be impaired easily, and the appearance will be impaired as well.

<Photocatalyst Layer>

A photocatalyst layer of the photocatalyst transfer film of the present invention contains a titanium oxide particle-containing photocatalyst, antimicrobial metal-containing alloy particles, a silicon compound and a surfactant. Such photocatalyst layer can be formed by performing coating with a photocatalyst coating liquid containing a titanium oxide particle-containing photocatalyst, antimicrobial metal-containing alloy particles, a silicon compound, a surfactant and an aqueous dispersion medium.

Titanium Oxide Particle-Containing Photocatalyst

As for a photocatalyst, it is preferred that there be used a photocatalyst superior in transparency in view of design features after processing.

In this specification, the term "photocatalyst" is a collective term referring to a substance exhibiting a photocatalytic action when irradiated with a light having an energy not lower than a given bandgap. Examples of such substance include known metal oxide semiconductors such as titanium oxide, tungsten oxide, zinc oxide, tin oxide, iron oxide, bismuth oxide, bismuth vanadate and strontium titanate. As the photocatalyst used in the photocatalyst transfer film of the present invention, particles of any one kind of these substances may be used, or particles of two or more kinds of these substances may be used in combination. Particularly, it is preferred that there be used titanium oxide particles having an especially high photocatalytic action when irradiated with a light beam containing an ultraviolet light of a wavelength of not higher than 400 nm (preferably 280 to 380 nm), being chemically stable, allowing nanosized particles to be synthesized relatively easily, and being able to be relatively easily dispersed in a solvent of such nanosized particles.

As crystalline phases of titanium oxide particles, there are generally known three of them which are the rutile-type, anatase-type and brookite-type. It is preferred that there be used titanium oxide particles mainly composed of the anatase-type or rutile-type. Here, the expression "mainly composed" refers to an occupancy of usually not smaller than 50% by mass, preferably not smaller than 70% by mass, even more preferably not smaller than 90% by mass, or even 100% by mass in all the crystals of the titanium oxide particles.

As titanium oxide particles, there may be employed those with metal compounds of platinum, gold, palladium, iron, copper, nickel or the like being supported on titanium oxide particles, and those doped with elements such as tin, nitrogen, sulfur, carbon and transition metals, for the purpose of improving the photocatalytic activity of the particles. It is preferred that there be used titanium oxide particles doped with the above elements as particle size control will be easy, and a film superior in transparency will be able to be obtained.

In terms of transparency after coating, it is preferred that a titanium oxide particle dispersion liquid be used as the photocatalyst coating liquid for forming the photocatalyst layer. As the aqueous dispersion medium for the titanium oxide particle dispersion liquid, an aqueous solvent is normally used, and it is preferred that there be used water, a water-soluble organic solvent mixable with water, and a mixed solvent prepared by mixing water and a water-soluble organic solvent at any ratio. As water, preferred are, for example, a deionized water, a distilled water and a pure water. Moreover, as the water-soluble organic solvent, preferred are, for example, alcohols such as methanol, ethanol and isopropanol; glycols such as ethylene glycol; and glycol ethers such as ethylene glycol monomethyl ether, ethylene glycol monoethyl ether and propylene glycol-n-propyl ether. As the aqueous dispersion medium, any one kind of them may be used alone, or two or more kinds of them may be used in combination. If using the mixed solvent, it is preferred that a ratio between the water-soluble organic solvent and water be 1/10 to 15/10.

It is preferred that the titanium oxide particles in the titanium oxide particle dispersion liquid be fine particles. As for a dispersed particle size of such titanium oxide particles, a 50% cumulative distribution diameter $D_{50}$ on volume basis that is measured by a dynamic light scattering method using a laser light (possibly referred to as "average particle size" hereunder) is preferably 5 to 30 nm, more preferably 5 to 20 nm. This is because when the average particle size is smaller than 5 nm, an insufficient photocatalytic activity may be exhibited; and when the average particle size is greater than 30 nm, the dispersion liquid may turn non-transparent. Here, as a device for measuring the average particle size, there may be used, for example, ELSZ-2000ZS (by Otsuka Electronics Co., Ltd.), NANOTRAC UPA-EX150 (by Nikkiso Co., Ltd.), and LA-910 (by HORIBA, Ltd.).

It is preferred that the concentration of the titanium oxide particles in the titanium oxide particle dispersion liquid be 0.01 to 30% by mass, particularly preferably 0.3 to 20% by mass, in terms of ease in producing a later-described photocatalyst-alloy thin film having a given thickness.

Here, a method for measuring the concentration of the titanium oxide particle dispersion liquid may be such that part of the titanium oxide particle dispersion liquid is taken as a sample, followed by heating it at 105° C. for three hours so as to volatilize the solvent, and then calculating the concentration in accordance with the following formula based on the mass of the non-volatile content (titanium oxide particles), and the mass of the sampled titanium oxide particle dispersion liquid before heating.

Concentration of titanium oxide particle dispersion liquid (% by mass)=[mass of non-volatile content (g)/mass of titanium oxide particle dispersion liquid before heating (g)]×100

Antimicrobial Metal-Containing Alloy Particles

In the present invention, the alloy particles are comprised of at least two kinds of metal components, and contain at least one kind of antimicrobial metal.

The term "antimicrobial metal" refers to metals that are harmful to microorganisms such as bacteria and fungi (molds), but are relatively less harmful to the human body; examples of such metals include silver, copper, zinc, platinum, palladium, nickel, aluminum, titanium, cobalt, zirconium, molybdenum and tungsten that are known to reduce the viable count of *Staphylococcus aureus* and *E. coli* in a specification test for antimicrobial products JIS Z 2801 when used as metal component particles to coat a film (references 1 and 2 as below).

It is preferred that the alloy particles used in the photocatalyst transfer film of the present invention contain at least one of these metals, particularly preferably at least one of silver, copper and zinc.

Reference 1: Miyano, Iron and steel, 93(2007)1, 57-65
Reference 2: H. Kawakami, ISIJ Intern., 48(2008)9, 1299-1304

More specifically, the alloy particles may be those comprised of combinations of metal components, such as silver-copper, silver-palladium, silver-platinum, silver-tin, gold-copper, silver-nickel, silver-antimony, silver-copper-tin, gold-copper-tin, silver-nickel-tin, silver-antimony-tin, platinum-manganese, silver-titanium, copper-tin, cobalt-copper, zinc-magnesium, silver-zinc, copper-zinc and silver-copper-zinc.

There are no particular restrictions on the components in the alloy particles other than the antimicrobial metal(s); examples of such components may include gold, antimony, tin, sodium, magnesium, silicon, phosphorus, sulfur, potassium, calcium, scandium, vanadium, chromium, manganese, iron, gallium, germanium, arsenic, selenium, yttrium, niobium, technetium, ruthenium, rhodium, indium, tellurium, cesium, barium, hafnium, tantalum, rhenium, osmium, iridium, mercury, thallium, lead, bismuth, polonium, radium, lanthanum, cerium, praseodymium, neodymium, promethium, samarium, europium, gadolinium, actinium and thorium. Any one of them may be used alone, or two or more of them may be used in combination.

The antimicrobial metal(s) in the alloy particles are contained in an amount of 1 to 100% by mass, preferably 10 to 100% by mass, more preferably 50 to 100% by mass, with respect to the total mass of the alloy particles. This is because when the antimicrobial metal(s) are in an amount of smaller than 1% by mass with respect to the total mass of the alloy particles, an insufficient antimicrobial-antifungal capability may be exhibited.

It is preferred that an alloy particle dispersion liquid be used as the photocatalyst coating liquid for forming the photocatalyst layer. As the aqueous dispersion medium for the alloy particle dispersion liquid, an aqueous solvent is normally used; preferred are water, a water-soluble organic solvent mixable with water, or a mixed solvent prepared by mixing water and a water-soluble organic solvent at any ratio. As water, preferred are, for example, a deionized water, a distilled water and a pure water. Further, examples of the water-soluble organic solvent include alcohols such as methanol, ethanol, n-propanol, 2-propanol, n-butanol, 2-butanol, tert-butanol, ethylene glycol, diethylene glycol and polyethylene glycol; glycol ethers such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether and propylene glycol-n-propyl ether; ketones such as acetone and methyl ethyl ketone; water-soluble nitrogen-containing compounds such as 2-pyrrolidone and N-methylpyrrolidone; and ethyl acetate. Any one of them may be used alone, or two or more of them may be used in combination.

It is preferred that the alloy particles in the alloy particle dispersion liquid be fine particles. As for a dispersed particle size of such alloy particles, a 50% cumulative distribution diameter $D_{50}$ on volume basis that is measured by a dynamic light scattering method using a laser light (possibly referred to as "average particle size" hereunder) is preferably not larger than 200 nm, more preferably not larger than 100 nm, even more preferably not larger than 70 nm. There are no particular restrictions on the lower limit of the average particle size, and theoretically, even those having the minimum particle size enabling antimicrobial-antifungal property may be used. However, practically, it is preferred that the average particle size be not smaller than 1 nm. Further, it is not preferable when the average particle size is greater than 200 nm, because the dispersion liquid may turn non-transparent. Here, as a device for measuring the average particle size, there may be used, for example, ELSZ-2000ZS (by Otsuka Electronics Co., Ltd.), NANOTRAC UPA-EX150 (by Nikkiso Co., Ltd.), and LA-910 (by HORIBA, Ltd.).

There are no particular restrictions on the concentration of the alloy particles in the alloy particle dispersion liquid. However, in general, the lower the concentration is, the better the dispersion stability becomes. Thus, it is preferred that the concentration be 0.0001 to 10% by mass, more preferably 0.001 to 5% by mass, even more preferably 0.01 to 1% by mass. It is not preferable when the concentration is lower than 0.0001% by mass, because the productivity of the photocatalyst transfer film will decrease in a significant manner.

Silicon Compound

The silicon compound contained in the photocatalyst layer of the photocatalyst transfer film of the present invention is used as a binder in the photocatalyst layer.

Here, a "silicon compound-based binder" refers to a colloid dispersion, solution or emulsion of a silicon compound that is provided in a way such that a solid or liquid silicon compound is contained in an aqueous dispersion medium. Specific examples of such silicon compound-based binder include a colloidal silica (preferable average particle size 1 to 150 nm); solutions of silicates; silane, siloxane hydrolysate emulsions; silicone resin emulsions; and emulsions of copolymers of silicone resins and other resins, such as a silicone-acrylic resin copolymer and a silicone-urethane resin copolymer. Particularly, it is preferred that there be used a solution of silicates that is obtained by hydrolytic condensation of a tetrafunctional silicon compound under the presence of a basic compound. Examples of the tetrafunctional silicon compound include amorphous silica, silicon tetrachloride, tetraethoxysilane and tetramethoxysilane. Further, it is preferred that the basic compound be an organic ammonium salt, specific and preferable examples of which include tetramethylammonium hydroxide, triethylammonium hydroxide, tetrabutylammonium hydroxide and ethyltrimethylammonium hydroxide. The hydrolytic condensation reaction of the tetrafunctional silicon compound is performed in an aqueous medium and under the presence of a basic compound at a temperature of normal temperature to 170° C., using, as a raw material, the tetrafunctional silicon compound in an amount of preferably 1 to 20% by mass, more preferably 1 to 15% by mass with respect to a reaction system (raw material mixed liquid). It is preferred that the basic compound be added in an amount of not smaller than 100 mol %, more preferably 100 to 500 mol %, with respect to the tetrafunctional silicon compound.

When the tetrafunctional silicon compound is silica, it is preferable to prepare a raw material mixed liquid having a $SiO_2$ concentration of 1 to 15% by mass, a basic compound concentration of 2 to 25% by mass and water as a remainder, and then heat and stir such mixed liquid at 80 to 130° C.

Surfactant

Examples of the surfactant contained in the photocatalyst layer of the photocatalyst transfer film of the present invention include anionic surfactants such as fatty acid sodium salt, alkylbenzene sulfonate, higher alcohol sulfate ester salt and polyoxyethylene alkyl ether sulfate salt; cationic surfactants such as alkyltrimethyl ammonium salt, dialkyldimethyl ammonium salt, alkyldimethylbenzyl ammonium salt and quaternary ammonium salt; amphoteric surfactants such as alkylamino fatty acid salt, alkyl betaine and alkylamine oxide; and non-ionic surfactants such as polyoxyethylene alkyl ether, polyoxyethylene alkylphenol ether, alkyl glucoside, polyoxyethylene fatty acid ester, sucrose fatty acid ester, sorbitan fatty acid ester, polyoxyethylene sorbitan fatty acid ester, fatty acid alkanolamide and an acetylene-based surfactant. Among these examples, non-ionic surfactants are preferred in terms of stability of the coating liquid.

Further, a surfactant with an HLB value of 7 to 18 is preferred, and a surfactant with an HLB value of 10 to 15 is even more preferred. Particularly, an acetylene-based surfactant is preferred in terms of dispersibility, and a surfactant represented by the following general formula is more preferred.

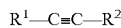

$$R^1-C\equiv C-R^2$$

Each of $R^1$ and $R^2$ independently represents a monovalent organic group, preferably a hydrocarbon group with part of its hydrogen atoms being substituted by an OH group(s), and having 1 to 20 carbon atoms. Moreover, each of $R^1$ and $R^2$ may also be a hydrocarbon group having 1 to 20 carbon atoms, but with part of the hydrocarbon group having an ether bond(s). Examples of an acetylene-based surfactant include OLFINE EXP4001, EXP4200, EXP4123 and EXP4300 (by Nissin Chemical Industry Co., Ltd.).

Method for Preparing Photocatalyst Coating Liquid

The photocatalyst coating liquid for forming the photocatalyst layer of the photocatalyst transfer film of the present invention can be prepared by mixing together the two kinds of particle dispersion liquids which are the titanium oxide particle dispersion liquid and the alloy particle dispersion liquid, and then adding a silicon compound and a surfactant thereto.

As described above, a titanium oxide-alloy particle dispersion liquid in the present invention is obtained by mixing together the two kinds of particle dispersion liquids which are the titanium oxide particle dispersion liquid and the antimicrobial-antifungal metal-containing alloy particle dispersion liquid that have been produced separately.

The two kinds of particle dispersion liquids which are the titanium oxide particle dispersion liquid and the antimicrobial-antifungal metal-containing alloy particle dispersion liquid can be produced by a method including the following steps (1) to (6).

(1) Step of producing a peroxotitanic acid solution from a raw material titanium compound, a basic substance, hydrogen peroxide and an aqueous dispersion medium.

(2) Step of obtaining the titanium oxide particle dispersion liquid by heating the peroxotitanic acid solution produced in the step (1) at 80 to 250° C. under a controlled pressure.

(3) Step of producing a solution containing a raw material antimicrobial metal compound, and a solution containing a reductant for reducing such metal compound.

(4) Step of producing an alloy particle dispersion liquid by mixing the solutions produced in the step (3) which are the solution containing the raw material antimicrobial metal compound, and the solution containing the reductant for reducing such metal compound.

(5) Step of washing the alloy particle dispersion liquid produced in the step (4) with an aqueous dispersion medium by a membrane filtration method.

(6) Step of mixing the titanium oxide particle dispersion liquid obtained in the step (2) and the alloy particle dispersion liquid obtained in the step (5).

The steps (1) and (2) are steps for producing the titanium oxide particle dispersion liquid.

The steps (3) to (5) are steps for producing the alloy particle dispersion liquid. While there are various physical and chemical methods, these production steps particularly employ a liquid phase reduction method which is a chemical method having advantages in terms of ease in adjusting synthesis conditions, wider controllable ranges of, for example, composition, particle size and particle size distribution, and productivity of the alloy particles. In such liquid phase reduction method, alloy particles are to be precipitated by mixing a reductant into a solution containing at least two kinds of metal ions serving as alloy raw materials. At that time, by allowing a protective agent of the alloy particles to coexist in the reaction system, the dispersibility of the alloy particles in the solvent can also be further improved.

The step (6) is a step for finally producing the titanium oxide-alloy particle mixed dispersion liquid having a deodorant and antimicrobial property, by mixing the titanium oxide particle dispersion liquid obtained in the step (2) and the alloy particle dispersion liquid obtained in the step (5).

Each step is described in detail hereunder.

Step (1):

In the step (1), the peroxotitanic acid solution is produced by reacting the raw material titanium compound, the basic substance and hydrogen peroxide in the aqueous dispersion medium.

As a method for producing the peroxotitanic acid solution, there may be employed a method where the basic substance is added to the raw material titanium compound in the aqueous dispersion medium to obtain titanium hydroxide, followed by eliminating impurity ions other than the metal ions contained, and then adding hydrogen peroxide thereto so as to obtain peroxotitanic acid; or a method where after adding hydrogen peroxide to the raw material titanium compound, the basic substance is then added thereto to obtain a peroxotitanium hydrate, followed by eliminating impurities other than the metal ions contained, and then further adding hydrogen peroxide thereto so as to obtain peroxotitanic acid.

Here, examples of the raw material titanium compound include titanium chlorides; inorganic acid salts such as nitrates and sulfates; organic acid salts such as formic acid, citric acid, oxalic acid, lactic acid and glycolic acid; and titanium hydroxides precipitated as a result of performing hydrolysis by adding alkalis to the aqueous solutions of these compounds. Any one of them may be used alone, or two or more of them may be used in combination. Particularly, as the raw material titanium compound, it is preferred that a titanium chloride(s) ($TiCl_3$, $TiCl_4$) be used.

As the aqueous dispersion medium, an aqueous dispersion medium similar to that in the titanium oxide particle dispersion liquid is used such that the aforementioned composition will be achieved. Here, the concentration of the raw material titanium compound aqueous solution comprised of the raw material titanium compound and the aqueous dispersion medium is not higher than 60% by mass, particularly preferably not higher than 30% by mass. While the lower limit of such concentration may be appropriately selected, it is preferred that the concentration be not lower than 1% by mass in general.

The basic substance is used to smoothly turn the raw material titanium compound into titanium hydroxide; examples of such basic substance include hydroxides of alkali metals or alkali earth metals, such as sodium hydroxide and potassium hydroxide; and amine compounds such as ammonia, alkanolamine and alkylamine. The basic substance is added in an amount at which the raw material titanium compound aqueous solution will have a pH level of not lower than 7, particularly 7 to 10. Here, the basic substance may also be used in the form of an aqueous solution having an appropriate concentration when combined with the aqueous dispersion medium.

Hydrogen peroxide is used to convert the raw material titanium compound or titanium hydroxide into peroxotitanium i.e. a titanium oxide compound containing a Ti—O—O—Ti bond, and is normally used in the form of a hydrogen peroxide water. It is preferred that hydrogen peroxide be added in an amount of 1.5 to 20 times larger than the substance quantity of titanium in terms of mole. Further, in the reaction where hydrogen peroxide is added to turn the raw material titanium compound or titanium hydroxide into peroxotitanic acid, it is preferred that a reaction temperature be 5 to 80° C., and that a reaction time be 30 min to 24 hours.

The peroxotitanic acid solution thus obtained may also contain an alkaline substance or an acidic substance for the purpose of pH adjustment or other purposes. Here, examples of the alkaline substance include ammonia, sodium hydroxide, calcium hydroxide and alkylamine.

Examples of the acidic substance include inorganic acids such as sulfuric acid, nitric acid, hydrochloric acid, carbonic acid, phosphoric acid and hydrogen peroxide; and organic acids such as formic acid, citric acid, oxalic acid, lactic acid and glycolic acid. In this case, it is preferred that the peroxotitanic acid solution obtained have a pH level of 1 to 9, particularly preferably 4 to 7 in terms of safety in handling.

Step (2):

In the step (2), the peroxotitanic acid solution obtained in the step (1) is subjected to a hydrothermal reaction at a temperature of 80 to 250° C., preferably 100 to 250° C. for 0.01 to 24 hours under a controlled pressure. An appropriate reaction temperature is 80 to 250° C. in terms of reaction efficiency and reaction controllability; as a result, the peroxotitanic acid will be converted into titanium oxide particles. Here, the expression "under a controlled pressure" refers to a state where when the reaction temperature employed is greater than the boiling point of the dispersion medium, pressure will be applied in an appropriate manner such that the reaction temperature can be maintained; as well as a state where when the reaction temperature employed is not higher than the boiling point of the dispersion medium, atmospheric pressure will be used for control. Here, the pressure is normally about 0.12 to 4.5 MPa, preferably about 0.15 to 4.5 MPa, more preferably 0.20 to 4.5 MPa. The reaction time is preferably 1 min to 24 hours. The titanium oxide particle dispersion liquid is obtained via this step (2).

While it is preferred that the particle size of the titanium oxide particles thus obtained be within the aforementioned range(s), the particle size can be controlled by adjusting the reaction conditions. For example, the particle size can be reduced by shortening the reaction time and a temperature rising time.

Step (3):

In the step (3), produced are the solution with the raw material antimicrobial metal compound being dissolved in an aqueous dispersion medium; and the solution with the reductant for reducing such raw material antimicrobial metal compound being dissolved in an aqueous dispersion medium.

As a method for producing these solutions, there may be employed a method where the raw material antimicrobial metal compound and the reductant for reducing such raw material antimicrobial metal compound are individually and separately added to an aqueous dispersion medium, followed by performing stirring so as to allow them to be dissolved therein. There are no particular restrictions on a stirring method as long as the method employed enables a uniform dissolution in the aqueous dispersion medium; a commonly available stirrer can be used.

Various antimicrobial metal compounds may be used as the raw material antimicrobial metal compound, examples of which include antimicrobial metal chlorides; inorganic acid salts such as nitrates and sulfates; organic acid salts such as formic acid, citric acid, oxalic acid, lactic acid and glycolic acid; and complex salts such as amine complex, cyano complex, halogeno complex and hydroxy complex. Any one of them may be used alone, or two or more of them may be used in combination. Particularly, it is preferred that chlorides and inorganic acid salts such as nitrates and sulfates be used.

There are no particular restrictions on the reductant; there can be used any kind of reductant capable of reducing the metal ions composing the raw material antimicrobial metal compound. Examples of the reductant include hydrazines such as hydrazine, hydrazine monohydrate, phenylhydrazine and hydrazinium sulfate; amines such as dimethylaminoethanol, triethylamine, octylamine and dimethylaminoborane; organic acids such as citric acid, ascorbic acid, tartaric acid, malic acid, malonic acid and formic acid; alcohols such as methanol, ethanol, isopropyl alcohol, ethylene glycol, diethylene glycol, triethylene glycol, tetraethylene glycol and benzotriazole; hydrides such as sodium borohydride, lithium borohydride, lithium triethylborohydride, lithium aluminum hydride, diisobutylaluminum hydride, tributyltin hydride, lithium tri(sec-butyl)borohydride, potassium tri (sec-butyl)borohydride, zinc borohydride and acetoxy sodium borohydride; pyrrolidones such as polyvinylpyrrolidone, 1-vinylpyrrolidone, N-vinylpyrrolidone and methylpyrrolidone; reducing sugars such as glucose, galactose, mannose, fructose, sucrose, maltose, raffinose and stachyose; and sugar alcohols such as sorbitol.

A protective agent may also be added to the solution with the reductant being dissolved in the aqueous dispersion medium. There are no particular restrictions on the protective agent as long as the protective agent employed is capable of preventing the alloy particles precipitated by reduction from agglutinating; there may be used a surfactant or an organic compound having a capability as a dispersant. Specific examples of the protective agent include surfactants such as anionic surfactants, cationic surfactants and nonionic surfactants; water-soluble polymer compounds such as polyvinylpyrrolidone, polyvinyl alcohol, polyethyleneimine, polyethylene oxide, polyacrylic acid and methylcellulose; aliphatic amine compounds such as ethanolamine, diethanolamine, triethanolamine and propanolamine; primary amine compounds such as butylamine, dibutylamine, hexylamine, cyclohexylamine, heptylamine, 3-butoxypropylamine, octylamine, nonylamine, decylamine, dodecylamine, hexadecylamine, oleylamine and octadecylamine; diamine compounds such as N,N-dimethylethylenediamine and N,N-diethylethylenediamine; and carboxylic acid compounds such as oleic acid.

As the aqueous dispersion medium (aqueous solvent), it is preferred that there be used water, a water-soluble organic solvent mixable with water, or a mixed solvent prepared by mixing water and a water-soluble organic solvent at any ratio. As water, preferred are, for example, a deionized water, a distilled water and a pure water. Further, examples of the water-soluble organic solvent include alcohols such as methanol, ethanol, isopropanol, n-propanol, 2-propanol, n-butanol, 2-butanol, tert-butanol, ethylene glycol and diethylene glycol; glycol ethers such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether and propylene glycol-n-propyl ether; ketones such as acetone and methyl ethyl ketone; water-soluble nitrogen-containing compounds such as 2-pyrrolidone and N-methylpyrrolidone; and ethyl acetate. As the aqueous dispersion medium, any one of them may be used alone, or two or more of them may be used in combination.

A basic substance or an acidic substance may be added to the aqueous dispersion medium. Examples of such basic substance include alkali metal hydroxides such as sodium hydroxide and potassium hydroxide; alkali metal carbonates such as sodium carbonate and potassium carbonate; alkali metal hydrogen carbonates such as sodium hydrogen carbonate and potassium hydrogen carbonate; alkali metal alkoxides such as potassium tert-butoxide, sodium methoxide and sodium ethoxide; alkali metal salts of aliphatic hydrocarbons such as butyl lithium; and amines such as triethylamine, diethylaminoethanol and diethylamine. Examples of the acidic substance include inorganic acids such as aqua regia, hydrochloric acid, nitric acid and sulfuric acid; and organic acids such as formic acid, acetic acid, chloroacetic acid, dichloroacetic acid, oxalic acid, trifluoroacetic acid and trichloroacetic acid.

There are no particular restrictions on the concentrations of the solution with the raw material antimicrobial metal compound being dissolved in the aqueous dispersion medium and the solution with the reductant for reducing such raw material antimicrobial metal compound being dissolved in the aqueous dispersion medium. However, there is a tendency that the lower these concentrations are, the smaller a primary particle size of each alloy particle formed will become. That is, it is preferred that a preferable concentration range(s) be determined based on the range of a target primary particle size.

There are no particular restrictions on the pH levels of the solution with the raw material antimicrobial metal compound being dissolved in the aqueous dispersion medium and the solution with the reductant for reducing such raw material antimicrobial metal compound being dissolved in the aqueous dispersion medium. It is preferred that the pH levels of these solutions be adjusted to preferable levels based on, for example, target molar ratios of the metals in the alloy particles and a target primary particle size.

Step (4):

In the step (4), the solution with the raw material antimicrobial metal compound being dissolved in the aqueous dispersion medium and the solution with the reductant for reducing such raw material antimicrobial metal compound being dissolved in the aqueous dispersion medium, which have been prepared in the step (3), are mixed to produce the alloy particle dispersion liquid.

There are no particular restrictions on a method for mixing these two solutions, as long as the method employed allows the two solutions to be uniformly mixed together. For example, there may be employed a method where the metal compound solution and the reductant solution are put into a reaction container before being stirred and mixed together; a method where stirring and mixing is performed in a way such that the reductant solution is delivered by drops into the metal compound solution already placed in a reaction container while stirring such metal compound solution; a method where stirring and mixing is performed in a way such that the metal compound solution is delivered by drops into the reductant solution already placed in a reaction container while stirring such reductant solution; or a method where the metal compound solution and the reductant solution are continuously supplied in constant amounts such that a reaction container or a microreactor, for example, may then be used to perform mixing.

There are no particular restrictions on a temperature at the time of preforming mixing; it is preferred that the temperature be adjusted to a preferable temperature based on, for example, target molar ratios of the metals in the alloy particles and a target primary particle size.

Step (5):

In the step (5), the alloy particle dispersion liquid produced in the step (4) is washed with an aqueous dispersion medium by a membrane filtration method.

As the aqueous dispersion medium, it is preferred that there be used water, a water-soluble organic solvent mixable with water, or a mixed solvent prepared by mixing water and a water-soluble organic solvent at any ratio. As water, preferred are, for example, a deionized water, a distilled water and a pure water. Further, examples of the water-soluble organic solvent include alcohols such as methanol, ethanol, isopropanol, n-propanol, 2-propanol, n-butanol, 2-butanol, tert-butanol, ethylene glycol and diethylene glycol; glycol ethers such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether and propylene glycol-n-propyl ether; ketones such as acetone and methyl ethyl ketone; water-soluble nitrogen-containing compounds such as 2-pyrrolidone and N-methylpyrrolidone; and ethyl acetate. As the water-soluble organic solvent, any one of them may be used alone, or two or more of them may be used in combination.

In the step (5), a membrane filtration method is used to wash and separate non-volatile impurities other than the alloy particles, such as components other than the metals in the raw material metal compound, the reductant and the protective agent, away from the alloy particle dispersion liquid produced in the step (4). It is preferred that washing be performed repeatedly until a mass ratio between the alloy particles and the non-volatile impurities in the alloy particle dispersion liquid (alloy particles/non-volatile impurities) has reached 0.01 to 10, more preferably 0.05 to 5, even more preferably 0.1 to 1. It is not preferable when the mass ratio is lower than 0.01, because there will be a large amount of impurities with respect to the alloy particles so that an antimicrobial, antifungal and deodorant properties imparted may not be fully exhibited; it is also not preferable when the mass ratio is greater than 10, because the dispersion stability of the alloy particles may deteriorate.

Determination of Metal Component Concentration in Alloy Particle Dispersion Liquid (ICP-OES)

The metal component concentration in the alloy particle dispersion liquid can be measured by appropriately diluting the alloy particle dispersion liquid with a pure water, and then introducing the diluted liquid into an inductively coupled plasma optical emission spectrometer (product name "Agilent 5110 ICP-OES" by Agilent Technologies, Inc.)

Determination of Non-Volatile Impurities Other Than Metal Components in Alloy Particle Dispersion Liquid Here, the concentration of the non-volatile impurities other than the metal components in the alloy particle dispersion liquid can be calculated by subtracting the metal component concentration determined by the above ICP-OES from a non-volatile content concentration that is calculated based on a mass of non-volatile contents (alloy particles+ non-volatile impurities) observed after the solvent has been volatilized as a result of heating part of the alloy particle dispersion liquid as a sample at 105° C. for three hours, and a mass of the sampled alloy particle dispersion liquid before heating.

Non-volatile impurity concentration (%)=[mass of non-volatile content (g)/mass of alloy particle dispersion liquid before heating (g)]×100-metal component concentration in alloy particle dispersion liquid (%)

There are no particular restrictions on a membrane used in the membrane filtration method, as long as the membrane used is capable of separating the alloy particles and the non-volatile impurities other than the alloy particles from the alloy particle dispersion liquid. Examples of such membrane include a microfiltration membrane, an ultrafiltration membrane and a nanofiltration membrane. Among these membranes, filtration can be carried out using a membrane having a suitable pore size.

As a filtration method, there may also be employed any of, for example, centrifugal filtration, pressure filtration and cross-flow filtration.

As for the shape of the filtration membrane, there may be appropriately employed those of, for example, a hollow-fiber type, a spiral type, a tubular type or a flat membrane type.

There are no particular restrictions on the material of the filtration membrane, as long as the material employed has a durability against the alloy particle dispersion liquid. The material may be appropriately selected from, for example, organic films such as those made of polyethylene, tetrafluoroethylene, difluoroethylene, polypropylene, cellulose acetate, polyacrylonitrile, polyimide, polysulfone and polyether sulfone; and inorganic films such as those made of silica, alumina, zirconia and titania.

Specific examples of the abovementioned filtration membrane include microza (by Asahi Kasei Chemicals Corporation), Amicon Ultra (by Merck Millipore Corporation), Ultra filter (by Advantec Toyo Kaisha, Ltd.) and MEMBRALOX (by Nihon Pall Ltd.).

Step (6):

In the step (6), the titanium oxide particle dispersion liquid obtained in the step (2) and the alloy particle dispersion liquid obtained in the step (5) are mixed to produce the titanium oxide-alloy particle mixed dispersion liquid having a deodorant and antimicrobial property.

There are no particular restrictions on a mixing method, as long as the method employed allows the two kinds of dispersion liquids to be uniformly mixed together; for example, mixing may be carried out by performing stirring using a commonly available stirrer.

A mixing ratio between the titanium oxide particle dispersion liquid and the alloy particle dispersion liquid in the photocatalyst coating liquid is 1 to 100,000, preferably 10 to 10,000, even more preferably 20 to 1,000, in terms of a particle mass ratio between the titanium oxide particles and the alloy particles in each dispersion liquid (titanium oxide particles/alloy particles). It is not preferable when the mass ratio is lower than 1, because the photocatalytic property will not be fully exhibited; it is also not preferable when the mass ratio is greater than 100,000, because the antimicrobial-antifungal capability will not be fully exhibited.

Here, as for a dispersed particle size of the mixture of the titanium oxide particles and the antimicrobial-antifungal metal-containing alloy particles in the titanium oxide-alloy particle dispersion liquid, a 50% cumulative distribution diameter $D_{50}$ on volume basis that is measured by a dynamic light scattering method using a laser light (possibly referred to as "average particle size" hereunder) is 5 to 100 nm, preferably 5 to 30 nm, more preferably 5 to 20 nm. This is because when the average particle size is smaller than 5 nm, an insufficient photocatalytic activity may be achieved; and when the average particle size is greater than 100 nm, the dispersion liquid may become non-transparent.

It is preferred that a silicon compound be added to the photocatalyst coating liquid in a way such that a mass ratio of silicon compound:titanium oxide particle will be 1:99 to 99:1, more preferably 10:90 to 90:10, even more preferably 30:70 to 70:30.

Next, the silicon compound-containing titanium oxide-alloy particle dispersion liquid is diluted with an aqueous dispersion medium in a way such that a concentration of the titanium oxide and the silicon compound will be 0.1 to 10% by mass, preferably 0.3 to 5% by mass.

As the aqueous dispersion medium, it is preferred that there be used water, a water-soluble organic solvent mixable with water, and a mixed solvent prepared by mixing water and a water-soluble organic solvent at any ratio. As water, preferred are, for example, a deionized water, a distilled water and a pure water. Moreover, as the water-soluble organic solvent, preferred are, for example, alcohols such as methanol, ethanol and isopropanol; glycols such as ethylene glycol; and glycol ethers such as ethylene glycol monomethyl ether, ethylene glycol monoethyl ether and propylene glycol-n-propyl ether. Alcohols are particularly preferred as a stable dispersibility will be achieved easily. It is preferred that a weight ratio of the water-soluble organic solvent/water in the mixed solvent be larger than 1/10, but not larger than 15/10; more preferably larger than 2/10, but not larger than 12/10.

A surfactant is then added to the silicon compound-containing titanium oxide-alloy particle dispersion liquid that has been diluted, at a ratio of 0.0005 to 5% by mass, preferably 0.001 to 1% by mass, in terms of liquid weight ratio, thereby obtaining the photocatalyst coating liquid.

<Protective Layer>

In the case of the photocatalyst transfer film of the present invention, a protective layer formed of a silicon compound may be further provided on the photocatalyst layer. The silicon compound used in the protective layer may include those similar to the silicon compounds that are added to the photocatalyst layer as binders, specific examples of which include colloidal silica (preferable average particle size being 1 to 150 nm); solutions of silicates; silane, siloxane hydrolysate emulsions; silicone resin emulsions; and emulsions of copolymers of silicone resins and other resins, such as a silicone-acrylic resin copolymer and a silicone-urethane resin copolymer. Particularly, it is preferred that there be used a silicate solution prepared by hydrolytic condensation of a tetrafunctional silicon compound under the presence of a basic compound. Examples of such tetrafunctional silicon compound include amorphous silica, silicon tetrachloride, tetraethoxysilane and tetramethoxysilane. Further, it is preferred that the basic compound be an organic ammonium salt, specific examples of which include tetramethylammonium hydroxide, triethylammonium hydroxide, tetrabutylammonium hydroxide and ethyltrimethylammonium hydroxide.

[Method for Producing Photocatalyst Transfer Film]

In the present invention, a method for producing the photocatalyst transfer film is such that the abovementioned photocatalyst coating liquid is to be applied to a base film to form a film of the photocatalyst layer.

The photocatalyst coating liquid may be applied to the base film by a known method that has been technically established. Specifically, a film of the photocatalyst coating liquid is formed by utilizing a method such as a spray coating method, a wire bar method, a die coating method, a gravure coating method, a micro gravure coating method, an inkjet method, a spin coating method or a dip coating method, followed by drying the coating film at 70 to 150° C., preferably 80 to 130° C., thereby obtaining a flat and smooth photocatalyst transfer film.

The dried photocatalyst layer may have a thickness of 20 to 300 nm, preferably 40 to 150 nm. When the film thickness of the photocatalyst layer is smaller than 20 nm, the photocatalytic effect may be small. Further, when the film thickness of the photocatalyst layer is larger than 300 nm, the photocatalyst layer may not be able to remain as a film.

In addition, a silicon compound-containing protective layer may be further laminated on the photocatalyst layer; coating with a silicon compound as contained in an aqueous dispersion medium may be performed by a known method that has been technically established. Specifically, a film of the silicon compound is formed by utilizing a method such as a spray coating method, a wire bar method, a die coating method, a gravure coating method, a micro gravure coating method, an inkjet method, a spin coating method or a dip coating method, followed by drying the coating film at 70 to 150° C., preferably 80 to 130° C., thereby obtaining a flat and smooth photocatalyst transfer film with the silicon compound-containing protective layer being laminated on the outermost surface thereof.

The dried protective layer containing the silicon compound may have a thickness of 20 to 300 nm, preferably 40 to 150 nm. When the film thickness of the protective layer is smaller than 20 nm, the protective layer may not be able to fully function as a protective layer. Further, when the film thickness of the protective layer is larger than 300 nm, the protective layer may break easily such that it may not be able to remain as a film.

[Method for Using Photocatalyst Transfer Film]

<Base Material Having Photocatalyst on Surface>

The photocatalyst transfer film of the present invention can be used to form photocatalyst films on the surfaces of various base materials. Here, there are no particular restrictions on the base materials; examples of such base materials may include organic materials and inorganic materials. These materials may have various shapes depending on their purposes and intended uses.

Examples of the organic materials include synthetic resin materials such as a vinyl chloride resin (PVC), polyethylene (PE), polypropylene (PP), polycarbonate (PC), an acrylic resin, polyacetal, a fluorine resin, a silicone resin, a ethylene-vinyl acetate copolymer (EVA), acrylonitrile-butadiene rubber (NBR), polyethylene terephthalate (PET), polyethylene naphthalate (PEN), polyvinyl butyral (PVB), an ethylene-vinyl alcohol copolymer (EVOH), a polyimide resin, polyphenylene sulfide (PPS), polyetherimide (PEI), polyether ether imide (PEEI), polyether ether ketone (PEEK), a melamine resin, a phenolic resin and an acrylonitrile-butadiene-styrene (ABS) resin; natural materials such as natural rubbers; and semisynthetic materials of these synthetic resin materials and natural materials. These materials may already be processed into particular shapes and structures such as those of films, sheets or other molded products as well as laminated bodies.

Examples of the inorganic materials include non-metallic inorganic materials and metallic inorganic materials.

Examples of the non-metallic inorganic materials include glass, ceramics and stone materials. They may already be processed into various shapes such as those of tiles, glass products, mirrors, walls and design materials.

Examples of metallic inorganic materials include cast iron, steel, iron, iron alloys, aluminum, aluminum alloys, nickel, nickel alloys and zinc die-cast. They may already be plated with the above metallic inorganic materials or coated with the above organic materials, or even be used to plate the surfaces of the above organic materials or non-metallic inorganic materials.

Further, a primer layer such as a silicone-based primer layer and an amine-based primer layer may be laminated on the surface of the base material; the primer layer makes transfer processing easy.

Base materials having the photocatalyst on the surfaces thereof include a base material used as an interior architectural material, such as a wall material, a wall paper, a ceiling material, a floor material, tiles, bricks, a wooden board, a resin board, a metallic plate, a tatami mat, a bathroom material and a melamine board for use in architectural structures; a base material used as, for example, a wall material, a ceiling material, a floor material, a seat, a handrail or a hanging strap for use in an automobile, trains and the like; a material for household furniture and living-ware-related products such as curtains, a blind, a rug, a partition board, a glass product, a mirror, a film, a desk, a chair, a bed and a storage rack; a material for home electric appliances such as an air cleaner, an air conditioner, a refrigerator, a laundry machine, a personal computer, a printer, a tablet, a touch panel and a telephone set; as well as a base material used in, for example, a signboard and a film.

<Method for Laminating Photocatalyst Film on Base Material>

While the photocatalyst transfer film of the present invention can be processed and thus transferred to the above base materials by a known method, a laminating method and a pressing method are preferred as they allow the photocatalyst layer to be transferred uniformly. Although depending on the properties of the transfer base material side, it is preferred that the film forming process be performed at a processing temperature of 110 to 170° C., particularly preferably 120 to 160° C., for about 5 min to 2 hours. When the processing temperature is lower than 110° C., the photocatalyst layer may not be able to be transferred to the transfer base material side. When the processing temperature is greater than 170° C., photocatalytic properties may not be achieved as the base film of the photocatalyst transfer film will be transferred to the transfer base material side and cover the surface of the photocatalyst layer.

Here, in the present invention, a protective film can be further formed on the surface of the photocatalyst layer formed on the base film, or on the surface of the protective layer.

There, while any film may be used as the protective film, the aforementioned plastic film may be used as the protective film.

A laminated body with such protective film being formed thereon can, for example, be easily transported when formed into the shape of a roll by a roller.

WORKING EXAMPLES

The present invention is described in detail hereunder with reference to working and comparative examples. However, the present invention is not limited to the following working examples.

(1) Measurement of Photocatalyst Layer Element (Elemental Analysis)

In order to confirm the transfer of the photocatalyst layer to the transfer base material side, each sample obtained in the following working and comparative examples was cut into a size of 5 cm×5 cm, followed by using an energy dispersive X-ray fluorescence analyzer (XRF, EDX-7000 by Shimadzu Corporation) to perform X-ray fluorescence analysis on both the Ti element and Si element that are present on the transfer base material. As for each element, "○" was given when the element was detected, whereas "-" was given when the element was not detected. The results thereof are shown in Table 1.

(2) Hydrophilicity Evaluation (Water Contact Angle Measurement)

In order to confirm the effect of the photocatalyst, each sample obtained in the following working and comparative examples was irradiated with an ultraviolet light, followed by using a contact angle meter (DM-501 by Kyowa Interface Science Co., Ltd.) to measure the water contact angle of each sample. The results thereof are shown in Table 1.

(3) Appearance (Transparency)

The appearance of each sample obtained in the following working and comparative examples was visually confirmed; "×" was given when white turbidity was confirmed due to ununiform transfer, whereas "○" was given when transparency was confirmed to have been maintained. The results thereof are shown in Table 1.

(4) Smoothness

An arithmetic average roughness Ra of the surface of the base film of the photocatalyst transfer film was measured by a 3D laser microscope (OLS-4000 by Nikon Corporation). Average values (n=3) are shown in Table 1.

(5) Antimicrobial Capability (Dark Place, E. coli)

Each sample obtained in the following working and comparative examples was subjected to a test carried out by a method based on a method for testing a hybrid photocatalyst-processed plate-shaped product, as described in "Fine ceramics (advanced ceramics, advanced technical ceramics)—Test method for antibacterial activity of photocatalytic products and efficacy" of Japanese Industrial Standards, JIS R 1702:2012. Antimicrobial activity values were calculated, and evaluation was conducted by the criteria shown below.

Very favorable (graded A) . . . antimicrobial activity value was not lower than 4.0.

Favorable (graded B) . . . antimicrobial activity value was not lower than 2.0.

Unfavorable (graded C) . . . antimicrobial activity value was lower than 2.0.

(5) Average Particle Size $D_{50}$

An average particle size $D_{50}$ of the particles in the titanium oxide particle dispersion liquid, the alloy particle dispersion liquid as well as the mixture of the two kinds of particles which were the titanium oxide particles and the alloy particles, was calculated as a 50% cumulative distribution diameter on volume basis that was measured by a dynamic light scattering method using a laser light, and with the aid of ELSZ-2000ZS (by Otsuka Electronics Co., Ltd.).

<Preparation of Silicon Compound-Containing Liquid α>

An amorphous silica, water and ethyltrimethylammonium hydroxide (20% by mass aqueous solution by SACHEM Japan Godo Kaisha) were mixed together in a way such that a ratio between silica and ethyltrimethylammonium hydroxide would be silica: ethyltrimethylammonium hydroxide=1:2 (molar ratio), and that a silica content in the system at the beginning of the reaction would be 5% by mass, followed by stirring them for two hours while performing heating at 110° C. The solution obtained was then diluted with water so that a solid content concentration would be 0.5% by mass, followed by using an ion-exchange resin (product name: DOWEX 50W-X8 by Dow Corning Corp.) to adjust the pH level to 7.0, thereby obtaining a silicon compound-containing liquid α.

A silicon compound-containing liquid β was obtained in a similar manner as the preparation of the silicon compound-containing liquid α, except that the solid content concentration was adjusted to 1.0% by mass.

<Preparation of Titanium Oxide Particle Dispersion Liquid A>

After diluting a 36% by mass titanium chloride (IV) aqueous solution tenfold with a pure water, a 10% by mass ammonia water was then gradually added thereto to neutralize and hydrolyze the same, thereby obtaining a precipitate of titanium hydroxide. The precipitate-containing solution at that time had a pH level of 9. The precipitate obtained was then subjected to a deionization treatment where addition of pure water and decantation were performed repeatedly. A 35% by mass hydrogen peroxide water was then added to the deionized precipitate of titanium hydroxide in a manner such that a ratio of $H_2O_2/Ti$ (molar ratio) would become 5, followed by stirring them at room temperature for 24 hours for sufficient reaction, thereby obtaining a yellow and transparent peroxotitanic acid solution (a).

The peroxotitanic acid solution (a) of an amount of 400 mL was put into a 500 mL autoclave to be hydrothermally processed for 90 min under a condition of 130° C., 0.5 MPa, followed by performing concentration control by adding a pure water thereto, thereby obtaining a titanium oxide particle dispersion liquid A (non-volatile content concentration 1.0% by mass, average particle size $D_{50}$ 12 nm).

<Preparation of Titanium Oxide Particle Dispersion Liquid B>

A yellow and transparent peroxotitanic acid solution (b) doped with tin was obtained in a similar manner as the preparation of the titanium oxide particle dispersion liquid A, except that tin chloride (IV) was added to and dissolved into the 36% by mass titanium chloride (IV) aqueous solution in a way such that a ratio of Ti/Sn (molar ratio) would be 20.

The peroxotitanic acid solution (b) of an amount of 400 mL was put into a 500 mL autoclave to be hydrothermally processed for 90 min under a condition of 150° C., followed by performing concentration control by adding a pure water thereto, thereby obtaining a titanium oxide particle dispersion liquid B (non-volatile content concentration 1.0% by mass, average particle size $D_{50}$ 10 nm).

The crystalline phases of the titanium oxide particles in the titanium oxide particle dispersion liquids A and B obtained were identified by measuring the powder X-ray diffraction of a titanium oxide particle powders collected after drying each titanium oxide particle dispersion liquid at 105° C. for three hours, using a desktop X-ray diffraction device (product name "D2 PHASER" by Bruker AXS GmbH).

The crystalline phase of the titanium oxide in the titanium oxide particle dispersion liquid A was confirmed to be anatase-type; the crystalline phase of the titanium oxide in the titanium oxide particle dispersion liquid B was confirmed to be rutile-type.

<Preparation of Silver-Copper Alloy Particle Dispersion Liquid C>

With ethylene glycol being used as a solvent, a raw material metal compound-containing solution (i) was produced by dissolving therein silver nitrate and copper nitrate trihydrate in a way such that a concentration as Ag would become 2.50 mmol/L, and a concentration as Cu would become 2.50 mmol/L.

A reductant-containing solution (ii) was obtained by mixing 55% by mass of ethylene glycol and 8% by mass of a pure water, as solvents; 2% by mass of potassium hydroxide as a basic substance; 20% by mass of hydrazine monohydrate and 5% by mass of dimethylaminoethanol, as reductants; and 10% by mass of polyvinylpyrrolidone as a reductant/protective agent.

A liquid obtained by rapidly mixing 2 L of the raw material metal compound-containing solution (i) heated to 160° C. in a reactor and 0.2 L of the reductant-containing solution (ii) of a temperature of 25° C., was concentrated with the aid of an ultrafiltration membrane having a molecular weight cut-off of 10,000 (microza by Asahi Kasei Chemicals Corporation) and washed with a pure water, thereby obtaining a 0.1% by mass alloy particle dispersion liquid C with pure water being a dispersion medium thereof (average particle size $D_{50}$ 60 nm, ratio of antimicrobial metals in alloy particles 100% by mass).

<Preparation of Silver-Palladium Alloy Particle Dispersion Liquid D>

A 0.1% by mass alloy particle dispersion liquid D with pure water being a dispersion medium thereof (average particle size $D_{50}$ 53 nm, ratio of antimicrobial metals in alloy particles 100% by mass) was obtained in a similar manner as the preparation of the alloy particle dispersion liquid C, except that there was used, instead of the raw material metal compound-containing solution (i), a raw material metal compound-containing solution (iii) with ethylene glycol being a solvent, and with silver nitrate and a palladium nitrate dihydrate being dissolved therein in a way such that a concentration as Ag was 4.00 mmol/L, and a concentration as Pd was 1.00 mmol/L.

<Preparation of Photocatalyst Coating Liquid E>

The titanium oxide particle dispersion liquid A (average particle size 12 nm) and the alloy particle dispersion liquid C were mixed together in a way such that a mass ratio of the particles in each dispersion liquid (titanium oxide particles/alloy particles) would be 1,000, followed by further mixing the silicon compound-containing liquid a into such mixed liquid so that a ratio of titanium oxide:silicon compound would be 1:1 (mass ratio). A mixed solvent of water/isopropyl alcohol (weight ratio 6/4), as a dispersion medium, was then added to such mixed liquid in a way such that a concentration of the titanium oxide and silicon compound would be 0.5% by mass, thereby obtaining a silicon compound-containing dispersion liquid of the titanium oxide particles and the alloy particles. An average particle size $D_{50}$ of the particle mixture of the two kinds of particles which are the titanium oxide particles and the alloy particles in this dispersion liquid was 18 nm.

An acetylene-based surfactant (OLFINE EXP 4200, HLB 10 to 13 by Nissin Chemical Industry Co., Ltd.) was then added and mixed into such dispersion liquid by an amount of 0.02% by mass in terms of liquid weight ratio, thereby obtaining a photocatalyst coating liquid E.

<Preparation of Photocatalyst Coating Liquid F>

The titanium oxide particle dispersion liquid B (average particle size 10 nm) and the alloy particle dispersion liquid D were mixed together in a way such that a mass ratio of the particles in each dispersion liquid (titanium oxide particles/alloy particles) would be 1,000, followed by mixing the silicon compound-containing liquid a into such mixed liquid so that a ratio of titanium oxide:silicon compound would be 1:1 (mass ratio). A mixed solvent of water/isopropyl alcohol (weight ratio 5/5), as a dispersion medium, was then added to such mixed liquid in a way such that a concentration of the titanium oxide and silicon compound would be 0.4% by mass, thereby obtaining a silicon compound-containing dispersion liquid of the titanium oxide particles and the alloy particles. An average particle size $D_{50}$ of the particle mixture of the two kinds of particles which are the titanium oxide particles and the alloy particles in this dispersion liquid was 16 nm.

An acetylene-based surfactant (OLFINE EXP 4200, HLB 10 to 13 by Nissin Chemical Industry Co., Ltd.) was then added and mixed into such dispersion liquid by an amount of 0.03% by mass in terms of liquid weight ratio, thereby obtaining a photocatalyst coating liquid F.

<Preparation of Photocatalyst Coating Liquid G>

A photocatalyst coating liquid G was obtained in a similar manner as the photocatalyst coating liquid F, except that there was used the silicon compound-containing liquid (3, and the concentration of the titanium oxide and silicon compound was set to be 0.7% by mass.

<Preparation of Photocatalyst Coating Liquid H> (for Comparative Example)

The silicon compound-containing liquid a was mixed into the titanium oxide particle dispersion liquid A (average particle size 12 nm) so that a ratio of titanium oxide/silicon compound would be 1:1 (mass ratio). A mixed solvent of water/isopropyl alcohol (weight ratio 6/4), as a dispersion medium, was then added to such mixed liquid in a way such that a concentration of the titanium oxide and silicon compound would be 0.5% by mass, thereby obtaining a silicon compound-containing titanium oxide particle dispersion liquid.

An acetylene-based surfactant (OLFINE EXP 4200, HLB 10 to 13 by Nissin Chemical Industry Co., Ltd.) was then added and mixed into such dispersion liquid by an amount of 0.02% by mass in terms of liquid weight ratio, thereby obtaining a photocatalyst coating liquid H.

<Preparation of Photocatalyst Coating Liquid I> (for Comparative Example)

The titanium oxide particle dispersion liquid A (average particle size 12 nm) and the alloy particle dispersion liquid C were mixed together in a way such that a mass ratio of the particles in each dispersion liquid (titanium oxide particles/alloy particles) would be 1,000.

A mixed solvent of water/isopropyl alcohol (weight ratio 6/4), as a dispersion medium, was then added to such mixed liquid in a way such that a concentration of the titanium oxide would be 0.5% by mass, thereby obtaining a dispersion liquid of the titanium oxide particles and the alloy particles. An average particle size $D_{50}$ of the particle mixture of the two kinds of particles which are the titanium oxide particles and the alloy particles in this dispersion liquid was 18 nm.

An acetylene-based surfactant (OLFINE EXP 4200, HLB 10 to 13 by Nissin Chemical Industry Co., Ltd.) was then added and mixed into such dispersion liquid by an amount of 0.02% by mass in terms of liquid weight ratio, thereby obtaining a photocatalyst coating liquid I.

<Preparation of Photocatalyst Coating Liquid J> (for Comparative Example)

The titanium oxide particle dispersion liquid A (average particle size 12 nm) and the alloy particle dispersion liquid C were mixed together in a way such that a mass ratio of the particles in each dispersion liquid (titanium oxide particles/alloy particles) would be 1,000, followed by further mixing the silicon compound-containing liquid into such mixed liquid so that a ratio of titanium oxide:silicon compound would be 1:1 (mass ratio). A mixed solvent of water/isopropyl alcohol (weight ratio 6/4), as a dispersion medium, was then added to such mixed liquid in a way such that a concentration of the titanium oxide and silicon compound would be 0.5% by mass, thereby obtaining a photocatalyst coating liquid J as a dispersion liquid of the titanium oxide particles and the alloy particles.

Working Example 1

The photocatalyst coating liquid E was applied to a PET film as a base film (T60 by Toray Industries, Inc., 50 μm) via wire bar coating, followed by performing drying in a dryer at 90° C. for 10 min so as to remove water and isopropyl alcohol, thereby obtaining a photocatalyst transfer film having a photocatalyst layer with a thickness of 50 nm.

Next, in order to evaluate transferability, a laminating roller was used to laminate the photocatalyst transfer film on a PET film as the transfer base material (A4300 by TOYOBO CO., LTD.) under a condition of 160° C., 1 m/min, and in a manner such that the photocatalyst layer would come into contact with the PET film as the transfer base material. The PET film as the base film of the photocatalyst transfer film was then peeled away, thus obtaining a transfer base material PET film with the photocatalyst layer being transferred thereto (Sample E-1). The sample E-1 to which the photocatalyst layer had been transferred was then subjected to various evaluations, and the results thereof are shown in Table 1.

Working Example 2

A sample E-2 was produced and then subjected to various evaluations in a similar manner as the working example 1, except that a PET film (S10 by Toray Industries, Inc.) was used as the base film and the transfer base material.

Working Example 3

A sample E-3 was produced and then subjected to various evaluations in a similar manner as the working example 1, except that a melamine resin board was used as the transfer base material.

Working Example 4

A sample E-4 was produced and then subjected to various evaluations in a similar manner as the working example 1, except that an OPP film (TORAYFAN by Toray Industries, Inc., 60 μm) was used as the base film, and a laminating temperature at the time of performing transfer processing was set to be 140° C.

Working Example 5

A photocatalyst transfer film and a sample F-1 after transfer were produced and then subjected to various evaluations in a similar manner as the working example 1, except that the photocatalyst coating liquid F was used as the coating liquid.

Working Example 6

A photocatalyst transfer film with a 90 nm-thick photocatalyst layer being laminated thereon was produced in a similar manner as the working example 5, except that the photocatalyst coating liquid G was used as the coating liquid, and an OPP film (TORAYFAN by Toray Industries, Inc., 60 μm) was used as the base film. A sample G-1 after transfer was then produced and subjected to various evaluations in a similar manner as the working example 5.

Working Example 7

A photocatalyst transfer film was produced in a similar manner as the working example 5, except that an OPP film (TORAYFAN by Toray Industries, Inc., 60 μm) was used as the base film. The silicon compound-containing liquid a was further applied to the photocatalyst layer of this photocatalyst transfer film via wire bar coating, followed by performing drying in a dryer at 90° C. for 10 min so as to remove water, thereby obtaining a photocatalyst transfer film with a 50 nm-thick protective layer of the silicon compound being laminated on the photocatalyst layer. A sample F-2 after transfer was then produced and subjected to various evaluations in a similar manner as the working example 5.

Comparative Example 1

A photocatalyst transfer film and a sample H-1 after transfer were produced and then subjected to various evaluations in a similar manner as the working example 1, except that used as the coating liquid was the photocatalyst coating liquid H free of antimicrobial metal-containing alloy particles.

Comparative Example 2

A photocatalyst transfer film and a sample I-1 after transfer were produced in a similar manner as the working example 1, except that the silicon compound-free photocatalyst coating liquid I was used as the coating liquid. Evaluations failed to be performed as the sample after transfer had exhibited a significantly inferior surface property and appearance.

Comparative Example 3

Attempts were made to produce a photocatalyst transfer film in a similar manner as the working example 1 except that the surfactant-free photocatalyst coating liquid J was used as the coating liquid. Transfer failed, and evaluations after transfer failed to be performed accordingly, as liquid puddles occurred on the film surface at the time of drying, the coating film exhibited white turbidity, and an ununiform film was formed.

TABLE 1

|  |  | Working example 1 | Working example 2 | Working example 3 | Working example 4 | Working example 5 | Working example 6 |
|---|---|---|---|---|---|---|---|
| Base film | Type | PET film | PET film | PET film | OPP film | PET film | OPP film |
|  | Ra [μm] | 1.5 | 3 | 1.5 | 0.49 | 1.5 | 0.49 |
|  | Surface treatment | Untreated | Untreated | Untreated | Untreated | Untreated | Untreated |
| Photocatalyst coating liquid |  | E | E | E | E | F | G |
| Protective layer |  | Not provided | Not provided | Not provided | Not provided | Not provided | Not provided |
| Transfer condition (lamination) |  | 160° C. 1 m/min | 160° C. 1 m/min | 160° C. 1 m/min | 140° C. 1 m/min | 160° C. 1 m/min | 160° C. 1 m/min |
| Transfer base material |  | PET film (A4300) | PET film (S10) | Melamine resin board | PET film (A4300) | PET film (A4300) | PET film (A4300) |
| Photocatalyst transfer sample |  | E-1 | E-2 | E-3 | E-4 | F-1 | G-1 |
| Elemental analysis | Ti | ○ | ○ | ○ | ○ | ○ | ○ |
|  | Si | ○ | ○ | ○ | ○ | ○ | ○ |
| Water contact angle [degree] |  | 30 | 30 | 28 | 22 | 28 | 21 |
| Antimicrobial property | Antimicrobial activity value | 2.8 | 2.2 | 2.5 | 4.3 | 3.3 | 4.8 |
|  | Grade | B | B | B | A | B | A |
| Appearance (transparency) |  | ○ | ○ | ○ | ○ | ○ | ○ |

|  |  | Working example 7 | Comparative example 1 | Comparative example 2 | Comparative example 3 |
|---|---|---|---|---|---|
| Base film | Type | OPP film | PET film | PET film | PET film |
|  | Ra [μm] | 0.49 | 1.5 | 1.5 | 1.5 |
|  | Surface treatment | Untreated | Untreated | Untreated | Untreated |
| Photocatalyst coating liquid |  | F | H | I | J |
| Protective layer |  | Provided | Not provided | Not provided | Not provided |
| Transfer condition (lamination) |  | 160° C. 1 m/min | 160° C. 1 m/min | 160° C. 1 m/min |  |
| Transfer base material |  | PET film (A4300) | PET film (A4300) | PET film (A4300) |  |
| Photocatalyst transfer sample |  | F-2 | H-1 | I-1 |  |
| Elemental analysis | Ti | ○ | ○ | Evaluations failed to be performed as sample after transfer exhibited significantly inferior surface property and appearance. | Photocatalyst transfer film failed to be obtained as uniform film failed to be formed. |
|  | Si | ○ | ○ |  |  |
| Water contact angle [degree] |  | 20 | 52 |  |  |
| Antimicrobial property | Antimicrobial activity value | 4.5 | 0 |  |  |
|  | Grade | A | C |  |  |
| Appearance (transparency) |  | ○ | ○ |  | x |

As is clear from the comparative example 1, the antimicrobial capability in the dark place was confirmed to be insufficient with the aid of the photocatalyst alone. Further, as is clear from the comparative example 2, when the photocatalyst layer does not contain the silicon compound, an unstable film will be formed such that the appearance after transfer will significantly deteriorate; and as is clear from the comparative example 3, it is difficult to form a uniform film if using a surfactant-free coating liquid.

Meanwhile, as is clear from the working examples 1 to 7, the photocatalyst transfer film having the photocatalyst layer formed of the coating liquid containing the titanium oxide particle-containing photocatalyst, antimicrobial metal-containing alloy particles, silicon compound and surfactant, has a favorable transfer processability with respect to various transfer base materials, exhibits a high transparency and thus an excellent design property even after transfer, and allows there to be transferred a photocatalyst layer showing an antimicrobial property in dark places.

The invention claimed is:

1. A photocatalyst transfer film having, on a base film, a photocatalyst layer containing a titanium oxide particle-containing photocatalyst, antimicrobial metal-containing alloy particles, a silicon compound and a surfactant.

2. The photocatalyst transfer film according to claim 1, wherein the silicon compound is a hydrolysis condensate of a tetrafunctional silicon compound, the hydrolysis condensate being obtained under the presence of an organic ammonium salt.

3. The photocatalyst transfer film according to claim 1, wherein the surfactant is an acetylene-based surfactant.

4. The photocatalyst transfer film according to claim 1, wherein an antimicrobial metal contained in the antimicrobial metal-containing alloy particles is at least one of metal selected from the group consisting of silver, copper and zinc.

5. The photocatalyst transfer film according to claim 1, wherein the antimicrobial metal-containing alloy particles at least contain silver.

6. The photocatalyst transfer film according to claim 1, wherein the antimicrobial metal contained in the antimicrobial metal-containing alloy particles is in an amount of 1 to 100% by mass with respect to a total mass of the antimicrobial metal-containing alloy particles.

7. The photocatalyst transfer film according to claim 1, wherein a dispersed particle size of a particle mixture of the two kinds of particles which are the titanium oxide particles and the antimicrobial metal-containing alloy particles is 5 to 100 nm in terms of a 50% cumulative distribution diameter $D_{50}$ on volume basis that is measured by a dynamic light scattering method using a laser light.

8. The photocatalyst transfer film according to claim 1, wherein the photocatalyst layer has a thickness of 20 to 300 nm.

9. The photocatalyst transfer film according to claim 1, wherein the base film has a thickness of 12.5 to 100 μm.

10. The photocatalyst transfer film according to claim 1, wherein a protective layer containing a silicon compound is further laminated on the photocatalyst layer.

11. A method for producing a photocatalyst transfer film, comprising:
 applying a photocatalyst coating liquid to a base film, the photocatalyst coating liquid containing a titanium oxide particle-containing photocatalyst, antimicrobial metal-containing alloy particles, a silicon compound, a surfactant and an aqueous dispersion medium; and
 performing drying.

* * * * *